United States Patent [19]
Bracy et al.

[11] Patent Number: 5,749,878
[45] Date of Patent: May 12, 1998

[54] ENDOSCOPIC SCREW ANCHOR EXTRACTOR

[75] Inventors: Barton W. Bracy; Reinhold Schmieding, both of Naples, Fla.

[73] Assignee: Arthrex, Inc., Naples, Fla.

[21] Appl. No.: 804,210

[22] Filed: Feb. 21, 1997

[51] Int. Cl.⁶ .................................................. A61B 17/04
[52] U.S. Cl. ............................................ 606/104; 606/232
[58] Field of Search ..................................... 606/104, 232

[56] References Cited

U.S. PATENT DOCUMENTS

| | | | |
|---|---|---|---|
| 5,591,207 | 1/1997 | Coleman | 606/104 |
| 5,667,513 | 9/1997 | Torrie et al. | 606/104 |

FOREIGN PATENT DOCUMENTS 3538593  5/1987  Germany ............................. 606/104

OTHER PUBLICATIONS

Fracture Appliances, Stryker Screw Driver advertising brochure, p. 33, Feb. 1, 1947.

*Primary Examiner*—Gary Jackson
*Attorney, Agent, or Firm*—Ostrolenk, Faber, Gerb & Soffen, LLP

[57] ABSTRACT

A cannulated screw anchor extractor with a clear plastic outer sheath allows backing out of the screw anchor from bone into the inner cannulation of the clear, plastic sheath. The threads of the screw anchor purchase the inner cannulation of the sheath to secure the anchor for removal from within the body and avoid screw loss in soft tissue during extraction.

11 Claims, 3 Drawing Sheets

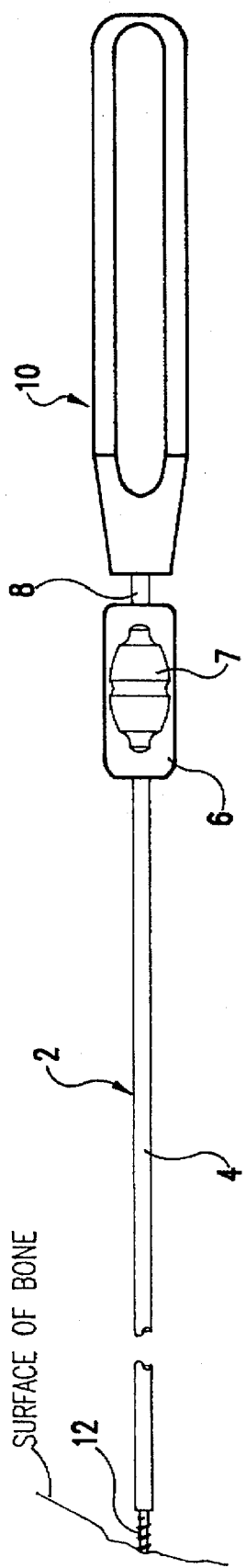
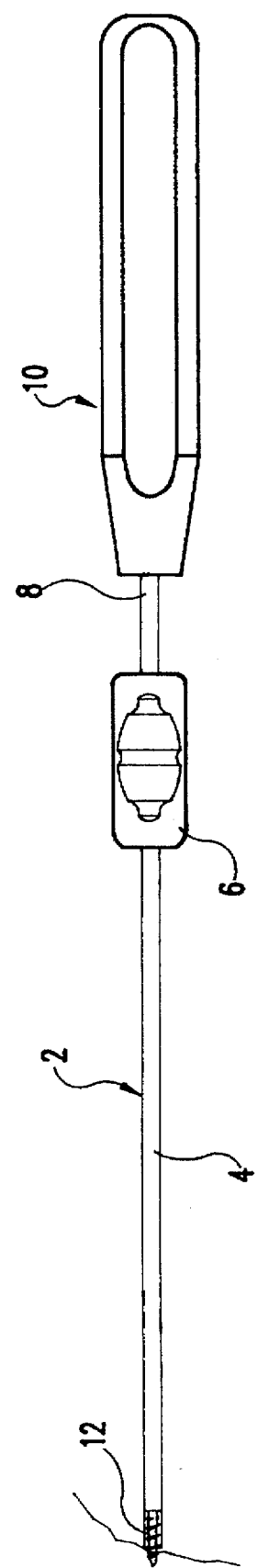
FIG. 1
FIG. 2

ENDOSCOPIC SCREW ANCHOR EXTRACTOR

This application claims the benefit of U.S. Provisional Application Ser. No. 60/012,090, filed Feb. 22, 1996.

BACKGROUND OF THE INVENTION

1. Field of the Invention

The present invention relates to an arthroscopic surgical method and apparatus for extracting a suture anchor from a human body.

2. Brief Description of the Related Art

Suture anchors are used in arthroscopic surgery to secure suture material to tissue. Various suture anchor assemblies have been developed. For example, U.S. Pat. No. 4,632,100 to Somers et al. and U.S. Pat. No. 4,898,156 to Gatturna et al. disclose suture anchors and tools for suture anchor installation. See also U.S. Pat. No. 4,899,743 to Nicholson et al., U.S. Pat. No. 5,370,662 to Stone et al., U.S. Pat. No. 5,466,243 to Schmieding et al., and U.S. Pat. No. 5,575,801 to Habermeyer et al. The disclosures of each of the above-identified patents are herein incorporated by reference.

After a suture anchor has been installed, it may become necessary to remove the suture anchor in certain circumstances. This can occur, for example, if the suture anchor has not been properly installed or has been installed in the wrong location. Although a simple hexagonal socket type driver can be mounted over the suture anchor and rotated counterclockwise to unseat the anchor from the bone, the anchor can separate from the driver and become lost as the driver is removed from the patient's body.

Accordingly, it is desirable to provide a device for engaging the suture anchor upon extraction to prevent the suture from becoming separated and lost.

SUMMARY OF THE INVENTION

The present invention overcomes the above-noted deficiency of the prior art by providing a hollow plastic extractor which is mounted over the shaft of a hexagonal socket type driver. The extractor is provided with a handle and can be slid over the suture anchor as it is being removed, such that the inner wall of the extractor engages and captures the suture anchor. The suture anchor can therefore be safely removed from the patient's body with reduced risk of separation and loss during the extraction procedure.

Other features and advantages of the present invention will become apparent from the following description of the invention which refers to the accompanying drawings.

BRIEF DESCRIPTION OF THE DRAWINGS

FIG. 1 is a plan view schematically illustrating a step in the method of suture anchor extraction using the suture anchor extractor of the present invention.

FIG. 2 is a plan view schematically illustrating a further step in the method of suture anchor extraction using the suture anchor extractor of the present invention.

DETAILED DESCRIPTION OF THE PREFERRED EMBODIMENTS

Figure 3:
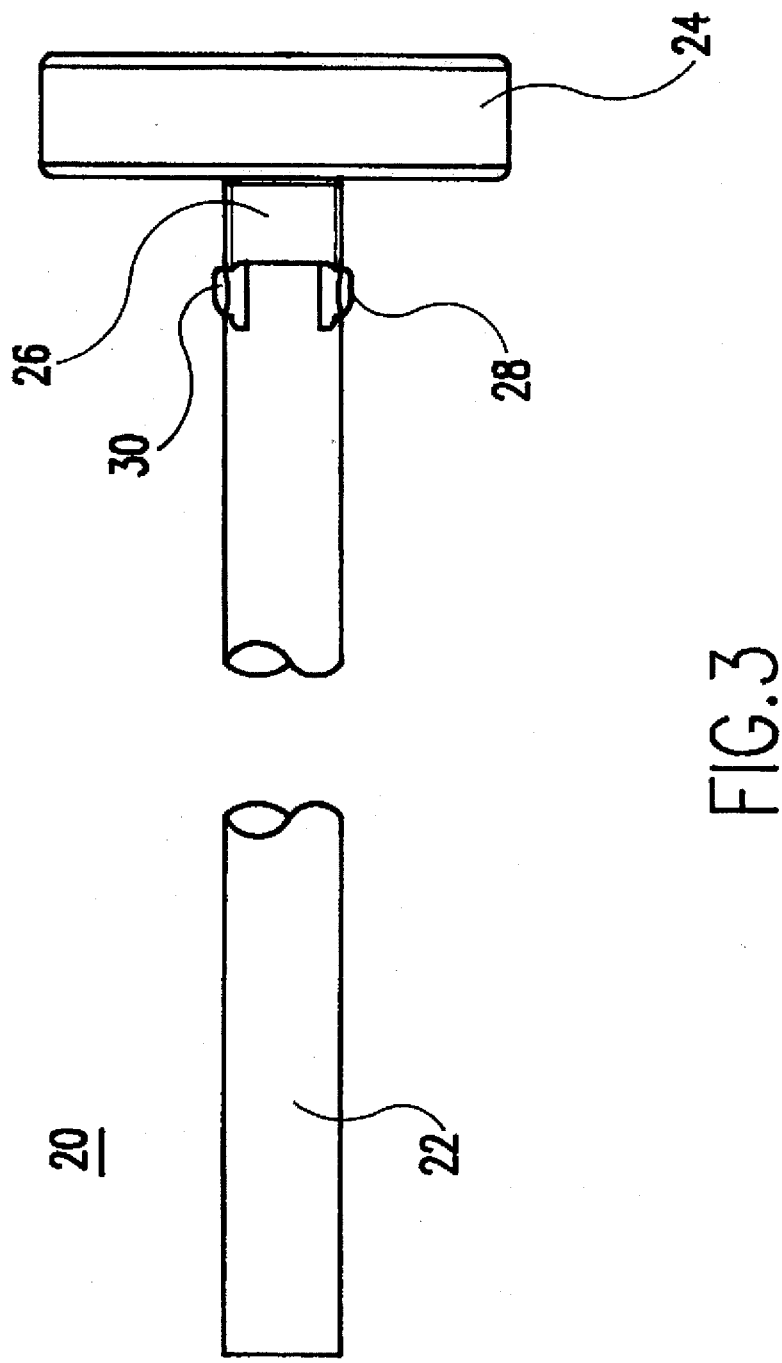
FIG. 3 is a side view of a tube for a suture anchor extractor according to an alternative embodiment of the present invention.

Referring to FIGS. 1 and 2, a suture anchor extractor 2 according to the present invention is shown. Extractor 2 comprises an elongated, clear plastic tube 4 provided at a proximal end with a cylindrical, oblong handle 6. Handle 6 includes a pair of opposed ridged finger grips 7 on its outer surface, only one of which is shown in FIGS. 1 and 2.

Tube 4 and handle 6 of extractor 2 are slidably received over a shaft 8 of a hexagonal socket-type driver 10. In FIGS. 1 and 2, the distal end of socket driver 10 is shown engaged with the head of a suture anchor 12. Suture anchor 12 is shown schematically as having been partially extracted from the bone tissue in which the anchor had been implanted.

A method of extracting a suture anchor according to the present invention is described with reference to FIGS. 1 and 2 as follows: Extractor 2 is disposed over shaft 8 of hexagonal socket driver 10 in a retracted position and the hexagonal socket at the distal end of driver shaft 8 is fully engaged with the hex on the back of suture anchor 12, such as a FASTak™ suture anchor sold by the assignee of the present application. In the position shown in FIG. 1, hexagonal driver 10 has been rotated counterclockwise until only 1–1½ threads remain in bone, and a sufficient length of the suture anchor is exposed for capture. Extractor 2 rotates with the driver.

Figure 4:
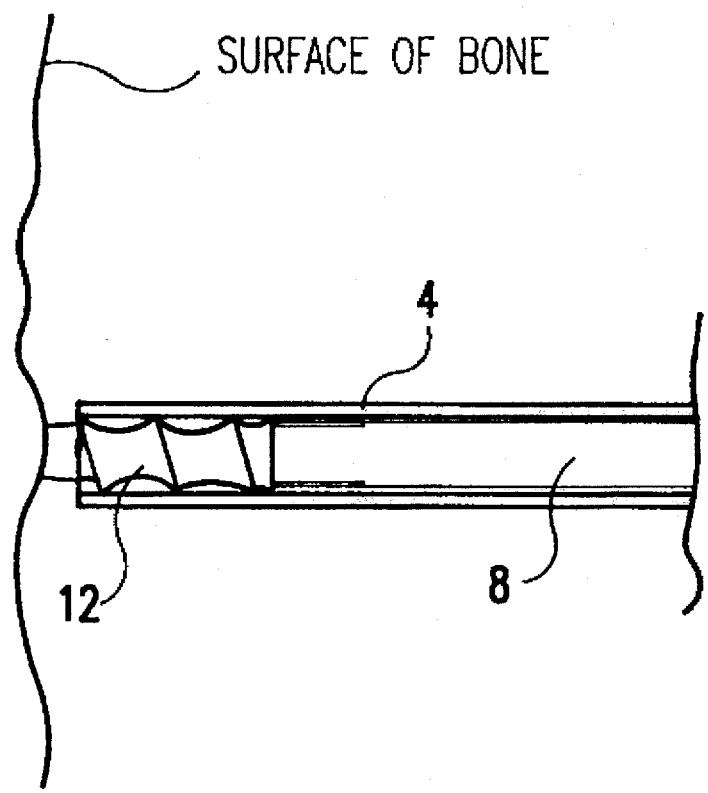
FIG. 4 is an enlarged detail view of the suture anchor and the distal end of the extractor assembly shown in FIG. 2.

Using handle 6, extractor tube 4 is then advanced along shaft 8 toward the bone surface until the distal end of the tube abuts the surface of the bone. As a result, the distal end of tube 4 extends beyond the distal end of shaft 8 and over the suture anchor, as shown in FIG. 2. The suture anchor becomes captured within the distal end of tube 4, the inner diameter of the tube being such that at least a portion of the outer diameters on the threads of the suture anchor engage the inside walls of tube 4, thereby frictionally securing the suture anchor within extractor 2. See FIG. 4.

Counterclockwise rotation of driver 10 then is continued until the suture anchor is completely disengaged from the bone. The driver, extractor, and suture anchor can then be safely removed from the joint with the suture anchor captured within the extractor, thereby reducing risk of loosing the anchor within the joint.

Referring to FIG. 3, an alternative screw anchor extractor 20 according the present invention is shown. Screw anchor extractor 20 is similar to extractor 2 described above, but has a larger diameter elongated clear plastic tube 22 to accommodate larger suture anchors, such as the Corkscrew™ suture anchor sold by the assignee of the present application. Screw anchor extractor 20 includes a button-type handle 24 which serves the same purpose as handle 6 of the first embodiment.

Handle 24 has a shank 26 which is provided with tabs 28, 30. In the assembly of extractor 20, shank 26 is received within tube 22 and tabs 28, 30 snap into corresponding cross holes (not shown) provided in the proximal end of tube 22. Screw anchor extractor 20 is used in a manner similar to that described above with respect to extractor 2.

Although the present invention has been described in relation to particular embodiments thereof, many other variations and modifications and other uses will become apparent to those skilled in the art. Therefore, the invention is to be limited not by the specific description above, but only by the appended claims.

What is claimed is:

1. A suture anchor extractor for capturing and extracting a suture anchor, the extractor comprising:

a suture anchor driver having elongated shaft with an outer shaft diameter and a distal end;

a suture anchor having threads and disposed on the distal end of the suture anchor driver;

an elongated cylindrical tube having a length extending over a portion of the shaft, the tube having a distal end and a proximal end, the tube having an inner diameter dimensioned such that the tube is disposed slidably over the shaft of the suture anchor driver to advance the tube such that the distal end of the tube extends beyond the distal end of the shaft to frictionally engage the threads of the suture anchor and thereby capture the suture anchor; and means for gripping the tube for facilitating longitudinal sliding of the tube along the shaft.

2. The suture anchor extractor of claim 1, wherein the distal end of the tube has a plastic inner wall surface for frictionally engaging the suture anchor.

3. The suture anchor extractor of claim 1, wherein the distal end of the tube is formed of clear plastic.

4. A suture anchor extractor for capturing and extracting a suture anchor, the extractor comprising:

a suture anchor driver having a shaft with an outer shaft diameter and a distal end;

tube having a distal end and a proximal end, the tube being disposed slidably over the shaft and having a plastic inner wall for frictionally engaging the suture anchor; and a finger grip provided on the tube for sliding the tube axially along the shaft.

5. The suture anchor extractor of claim 4, wherein the plastic inner wall on the distal end of the tube is for frictionally engaging threads on the suture anchor.

6. The suture anchor extractor of claim 4, wherein the distal end of the tube is translucent.

7. The suture anchor extractor of claim 4, wherein the shaft has a shaft length, and a length of the tube is less than the shaft length.

8. A method of extracting a suture anchor from bone comprising the steps of:

engaging the suture anchor to be extracted with a suture anchor driver, the driver including a shaft and an elongated tube disposed over the shaft;

rotating the suture anchor by turning the driver such that at least a portion of the suture anchor is exposed outside of the bone;

capturing the suture anchor by sliding the tube over the shaft of the driver so that the distal end of the tube engages the exposed portion of the suture anchor; and extracting the captured suture anchor from the bone.

9. The method of claim 8, wherein the suture anchor has threads, and the step of capturing the suture anchor comprises engaging the threads with the distal end of the tube.

10. The method of claim 8, wherein the step of rotating the suture anchor comprises turning the driver counter-clockwise.

11. The method of claim 10, wherein the step of extracting the captured suture anchor comprises turning the tube with the driver.

* * * * *